(12) United States Patent
Nakagawa et al.

(10) Patent No.: US 7,023,959 B2
(45) Date of Patent: Apr. 4, 2006

(54) X-RAY DIAGNOSTIC INSTRUMENT

(75) Inventors: Akira Nakagawa, Kyoto (JP); Hiroshi Miyata, Kyoto (JP); Toshiaki Nakamura, Atsugi (JP); Takahiro Kamitake, Atsugi (JP)

(73) Assignee: Shimadzu Corporation, Kyoto (JP)

( * ) Notice: Subject to any disclaimer, the term of this patent is extended or adjusted under 35 U.S.C. 154(b) by 87 days.

(21) Appl. No.: 10/394,205

(22) Filed: Mar. 24, 2003

(65) Prior Publication Data

US 2003/0198317 A1   Oct. 23, 2003

(30) Foreign Application Priority Data

Apr. 19, 2002   (JP) .............................. 2002-117178

(51) Int. Cl.
*H05G 1/64* (2006.01)

(52) U.S. Cl. ....................................................... 378/98

(58) Field of Classification Search ................ 378/62, 378/109–118, 98
See application file for complete search history.

(56) References Cited

U.S. PATENT DOCUMENTS

| 4,170,735 | A | * | 10/1979 | Codina et al. ................ 378/96 |
| 4,991,193 | A | * | 2/1991 | Cecil et al. .................. 378/117 |
| 5,142,559 | A | * | 8/1992 | Wielopolski et al. ........ 378/205 |
| 5,206,894 | A | * | 4/1993 | Makrinos et al. .............. 378/93 |
| 5,555,120 | A | * | 9/1996 | Telymonde et al. .......... 398/111 |
| 5,870,450 | A | * | 2/1999 | Khutoryansky et al. .... 378/197 |
| 6,091,195 | A | * | 7/2000 | Forrest et al. ............... 313/504 |
| 6,149,283 | A | * | 11/2000 | Conway et al. .............. 362/236 |
| 6,737,801 | B1 | * | 5/2004 | Ragle .......................... 313/506 |

\* cited by examiner

*Primary Examiner*—Craig E. Church
*Assistant Examiner*—Jurie Yun
(74) *Attorney, Agent, or Firm*—Manabu Kanesaka

(57) ABSTRACT

An x-ray diagnostic instrument for taking an X-ray photograph of a patient includes a condition detecting device for detecting a condition of the instrument; a display device for displaying light in multicolor or flushing light; a memory device for storing predetermined display mode data of the display device for each condition of the instrument; and a control device for controlling the display device based on the display mode data stored in the memory device corresponding to a result from the condition detecting device.

8 Claims, 5 Drawing Sheets

X-RAY DIAGNOSTIC INSTRUMENT

BACKGROUND OF THE INVENTION AND RELATED ART STATEMENT

The invention relates to an X-ray diagnostic instrument, such as an X-ray irradiation imaging apparatus, for medical facilities and the like. More specifically, this invention relates to a technique for precisely recognize conditions of the X-ray diagnostic instrument even from a location, away from the X-ray diagnostic instrument.

Conventionally, an X-ray diagnostic instrument used in hospitals includes a portable X-ray instrument for doctor's visit. Such an X-ray instrument includes an X-ray tube device for generating X-ray; a collimator for forming the X-ray in a predetermined shape and radiating the X-ray generated from the X-ray tube device; an X-ray control panel for carrying out operations of X-ray imaging; a supporting portion for vertically and rotatably supporting the X-ray tube device; a cart for carrying the instrument; a brake portion for stopping the instrument at a desired location; and a cassette box for storing a plurality of cassettes therein. The X-ray instrument is a compact and light device, and provides excellent mobility.

An operation of taking an X-ray photograph using the X-ray instrument will be explained. First, a target area of a patient is placed on a cassette taken out from the cassette box. The instrument is moved toward the patient and the X-ray tube device is aligned to irradiate the X-ray on the target area of the patient placed on the cassette. An operator operates the X-ray control panel to prepare the radiography. When the radiography is ready, the operator holds a hand switch connected to the instrument and moves away from the instrument, and then pushes the hand switch to carry out the radiography. Generally, since the operator carries out the radiography for a number of times in a day, the operator operates the hand switch away from the instrument in order to prevent excess X-ray exposure. When the radiography is completed, a doctor diagnoses the patient using an X-ray photograph of the target area of the patient.

However, the conventional instrument with the structure described above has the following problem.

In the conventional instrument, in order to show conditions of the instrument, various lighting display portions are provided in a display space of the X-ray control panel for showing radiography preparation completion, radiography on-going, warning, malfunction and the like. In this case, the respective lighting display portions are small to save the display space of the X-ray control panel. Thus, it is difficult to distinguish which lighting display portion on the X-ray control panel is on from a location away from the instrument. In other word, there has been a problem in distinguishing the conditions of the instrument.

In view of the above problem, the present invention has been made, and an object of the invention is to provide an X-ray diagnostic instrument, wherein the conditions of the X-ray diagnostic instrument can be precisely recognized even from a location away from the instrument.

Further objects and advantages of the invention will be apparent from the following description of the invention.

SUMMARY OF THE INVENTION

In order to attain the above objects, according to the first aspect of the invention, an x-ray diagnostic instrument for taking an X-ray photograph of a patient includes condition detecting means for detecting a condition of the instrument; display means for displaying at least one of multicolor light and flushing light; memory means for storing predetermined display mode data of the display means for each condition of the instrument; and control means for displaying and controlling the display means based on the display mode data stored in the memory means corresponding to a result from the condition detecting means.

According to the first aspect of the invention, the condition detecting means detects the condition of the X-ray diagnostic instrument, and the display means carries out at least one of the multicolor display and the flushing display. The memory means stores the predetermined display mode data of the display means for each condition of the X-ray diagnostic instrument, and the control means displays and controls the display means based on the display mode data stored in the memory means corresponding to the result from the condition detecting means. Therefore, the condition of the X-ray diagnostic instrument can be displayed by the display mode of the display means, i.e. a color of the light or flushing of the light. Thus, an operator can instantly recognize the condition of the X-ray diagnostic instrument precisely even from a location away from the instrument by watching the color or flushing of the display means.

According to the second aspect of the invention, in the X-ray diagnostic instrument of the first aspect, the condition detecting means detects at least one of conditions relating to an imaging operation of an X-ray imaging system, an extended/housed condition of the X-ray imaging system and malfunction of the instrument.

According to the second aspect of the invention, the condition detecting means detects at least one of the conditions relating to the imaging operation of the X-ray imaging system; the extended/housed condition of the X-ray imaging system; and the abnormal condition of the instrument, as the condition of the X-ray diagnostic instrument. Thus, it is possible to show the condition of the imaging operation of the X-ray imaging system, the extended/housed condition of the X-ray imaging system and the abnormal condition of the X-ray diagnostic instrument as the display modes of the display means, i.e. a color and flushing of the display means. Accordingly, the operator can instantly recognize the condition of the X-ray diagnostic instrument by watching the color or the flushing of the display means even from a location away from the instrument.

According to the third aspect of the invention, in the X-ray diagnostic instrument according to the first and second aspects of the invention, the display means is arranged so that a display panel thereof can be seen in a horizontal direction. According to the third aspect of the invention, the display panel of the display device can be seen in the horizontal direction, thereby attaining excellent visibility.

Incidentally, the present invention also relates to a method of displaying the conditions of the X-ray diagnostic instrument as follows.

A method of displaying the conditions of the X-ray diagnostic instrument for taking the X-ray photograph includes a condition detecting step of detecting a condition of the instrument; and a control step of controlling a display device for displaying a multicolor display or a flushing display corresponding to a predetermined display mode of the display device for each condition of the instrument based on a condition detected in the condition detecting process.

According to the method of displaying the conditions of the X-ray diagnostic instrument described above, in the condition detecting step, the condition of the X-ray diagnostic instrument is detected. In the control step, the display device for displaying at lease one of the multicolor display or the flushing display is controlled and displayed corresponding to the predetermined display mode of the display device for each condition of the X-ray diagnostic instrument. Thus, the condition of the X-ray diagnostic instrument can be displayed by the display mode of the display device, i.e. a color or flushing of the display device, so that the operator can instantly recognize the condition of the X-ray diagnostic instrument precisely even from a location away from the X-ray diagnostic instrument by watching the color or flushing of the display device.

DETAILED DESCRIPTION OF PREFERRED EMBODIMENTS

Figure 1:
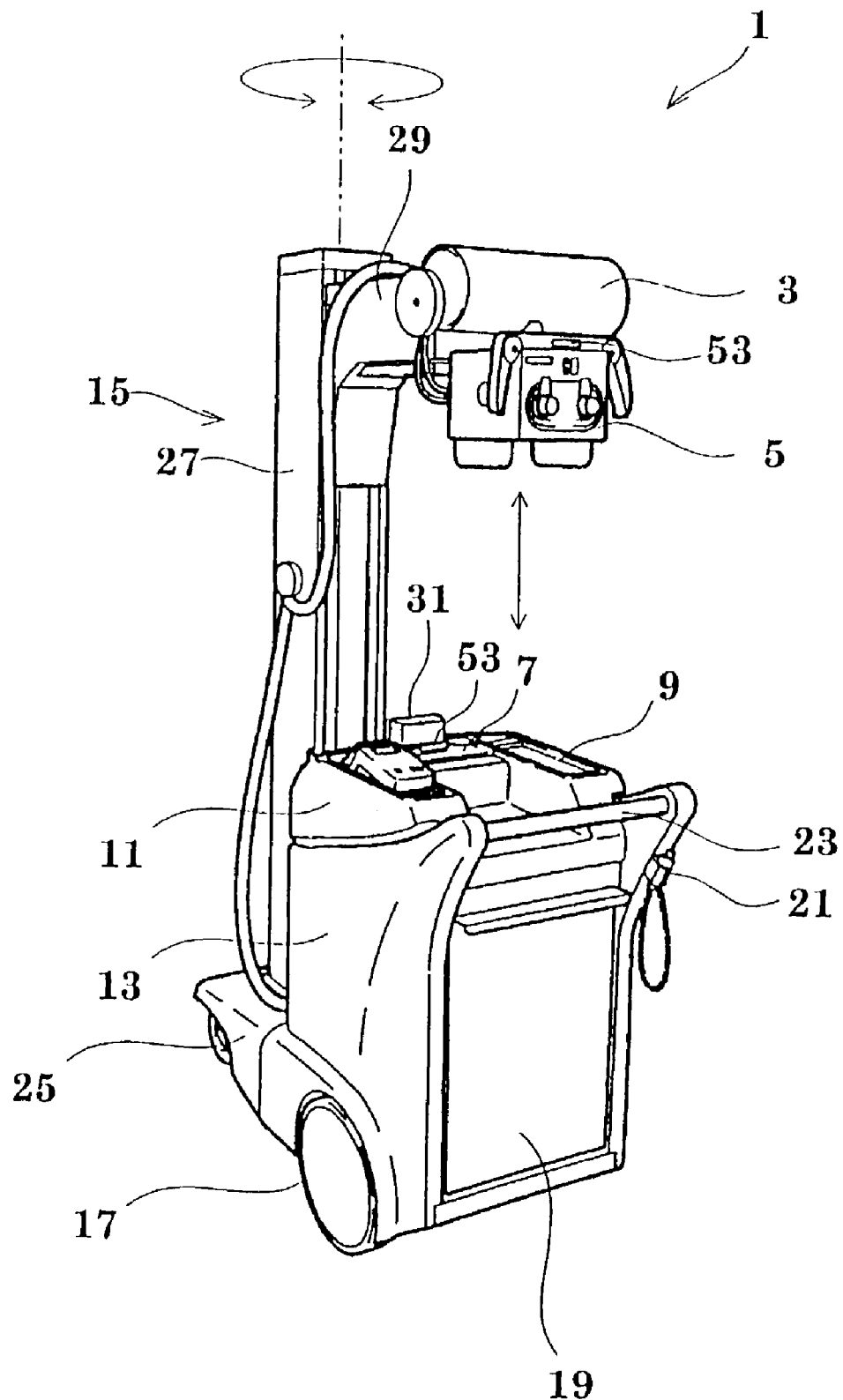
FIG. 1 is a perspective view of an X-ray diagnostic instrument according to an embodiment of the invention.
Figure 2:
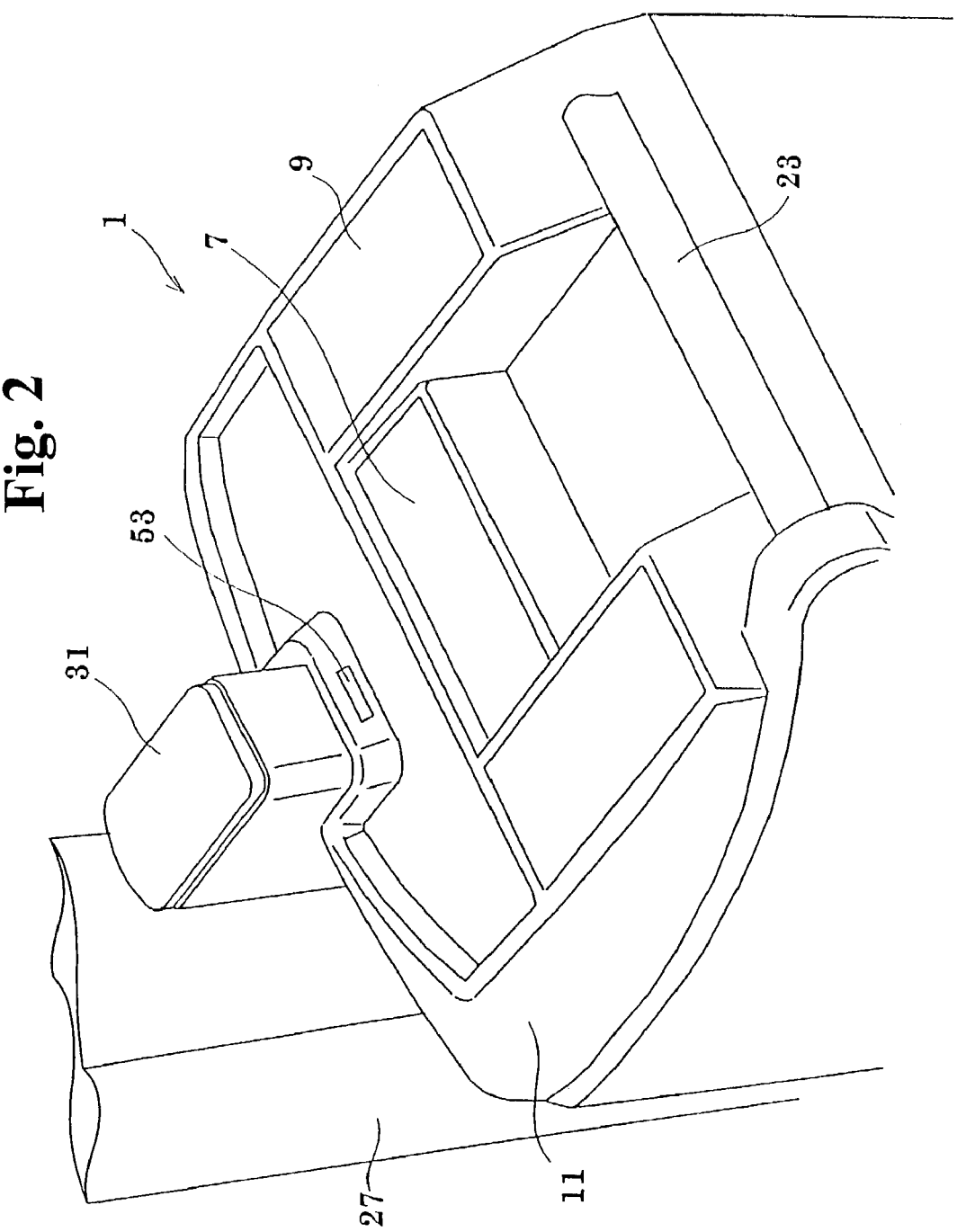
FIG. 2 is a perspective view of a cover portion of the X-ray diagnostic instrument.

Hereunder, embodiments of the present invention will be explained with reference to the accompanying drawings. FIG. 1 is a perspective view of an X-ray diagnostic instrument according to an embodiment; and FIG. 2 is a perspective view of a cover portion of the X-ray diagnostic instrument.

As shown in FIG. 1, an X-ray diagnostic instrument 1 (hereinafter, also referred as "instrument 1") includes an X-ray tube device 3 for generating X-ray; a collimator 5 for forming the X-ray generated by the X-ray tube device 3 in a predetermined shape and radiating the X-ray; an X-ray control panel 7 for performing operations of X-ray imaging; a power supply panel 9 for controlling on and off of a power supply of the instrument 1; a cover 11 including the X-ray control panel 7 and the power supply panel 9; a control portion 13 for controlling the instrument 1 based on an instruction from the X-ray control panel 7 and the power supply panel 9; a supporting portion 15 for supporting the X-ray tube device 3 rotatably and movably in the vertical direction; a cart 17 for carrying the instrument 1; a braking portion (not shown) for stopping or fixing the instrument 1 at a predetermined position; a cassette box 19 for storing a plurality (for example, 10 pieces) of cassettes; a hand switch 21 for starting the X-ray imaging from a location apart from the instrument 1; and a traveling handle 23 for an operator to hold and move the instrument. The X-ray instrument has a small size, a lightweight, and excellent mobility.

The X-ray instrument 1 is moved close to, for example, an object (hereinafter referred as "patient"), and the X-ray is irradiated to a target portion of the patient on a cassette, so that an X-ray photograph of the target portion can be taken. Hereunder, structures of various portions of the instrument 1 will be specifically explained.

The supporting portion 15 includes a rotary platform (not shown) disposed on a base portion 25 at a lower side of the instrument 1 so as to rotate within a predetermined angle (for example, within ±270° with respect to 0° as a standard position); a pole 27 vertically disposed on the rotary platform; and an arm 29 having one end supported by the pole 27 to be vertically movable and the other end provided with the X-ray tube device 3 and the collimator 5. As shown in FIG. 1, the standard position (0° position) is defined as a state that the X-ray tube device 3 and the collimator 5 face a side of the traveling handle 23. When the rotary platform (not shown) of the base portion 25 is rotated within a range of ±270° around the pole 27, the pole 27 itself is also rotated, thereby rotating the X-ray tube device 3 and the collimator 5 around the pole 27. Further, when the arm 29 is vertically moved along the pole 27, the X-ray tube device 3 and the collimator 5 can be moved vertically.

The operator can move the X-ray instrument 1 of the embodiment in a state that the arm 29 is lowered to an arm connecting portion 31, in other words, in a state that the arm 29 is housed. Also, a fitting portion (not shown) is provided at a portion corresponding to the arm 29 for inserting the arm connecting portion 31 therein. When the arm 29 is lowered so that the collimator 5 is housed in a depression of a cover 11 at a side of the traveling handle 23, the arm connecting portion 31 is fitted into the fitting portion (not shown) of the arm 29.

Figure 3:
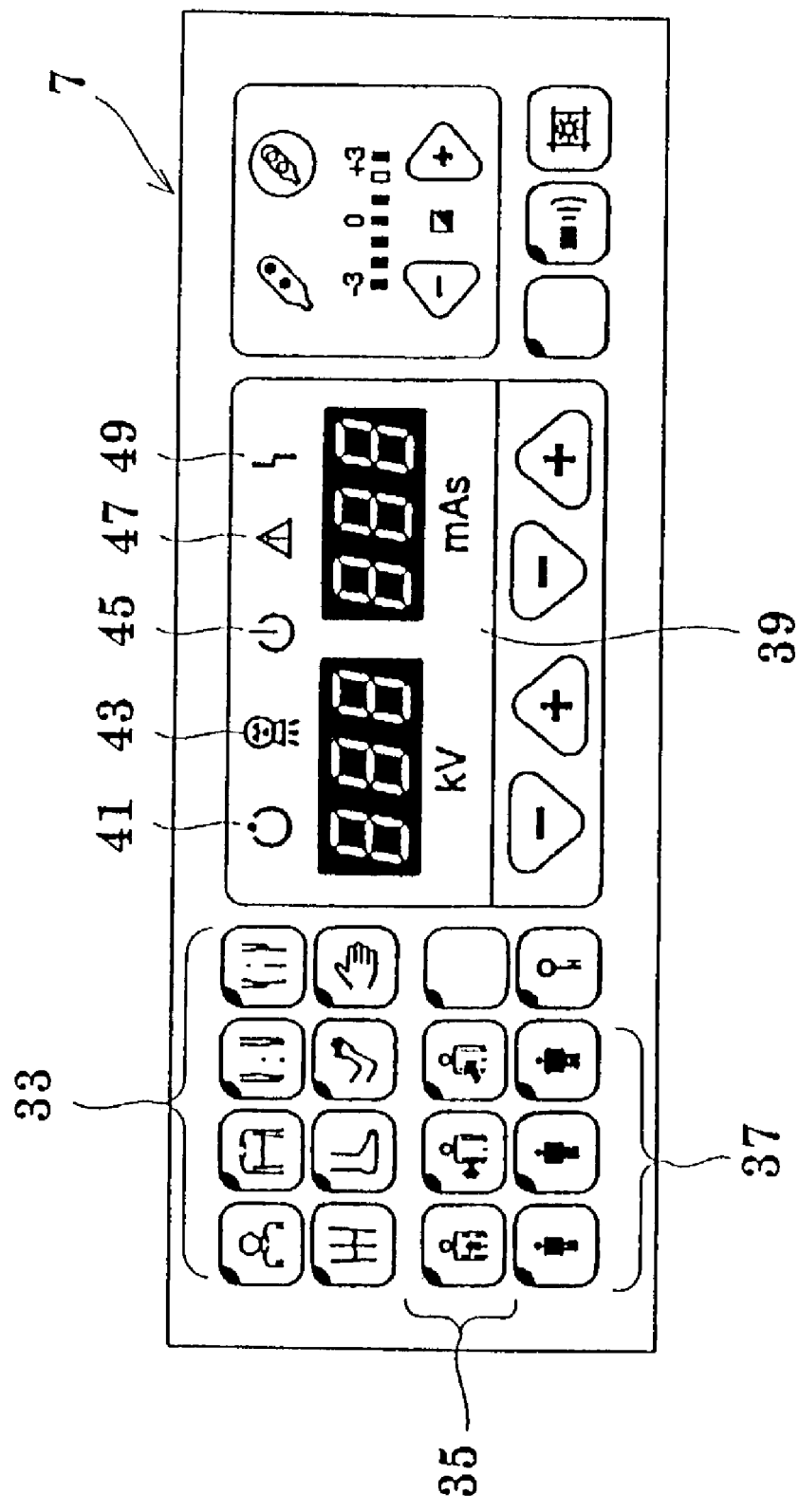
FIG. 3 is a plan view of a control panel of the X-ray diagnostic instrument.

The X-ray control panel 7 will be explained with reference to FIG. 3. FIG. 3 is a plan view showing the X-ray control panel. The X-ray control panel 7 includes position selection switches 33 for selecting and indicating a position of the patient where the X-ray is irradiated; X-ray direction selection switches 35 for selecting and indicating a X-ray direction relative to the patient; patient size selection switches 37 for selecting and indicating a physical size of the patient; a tube voltage/tube current display portion 39 for displaying values of an X-ray tube voltage and an X-ray tube current; an X-ray imaging preparation completion display 41 that turns on when the X-ray imaging preparation is completed; an X-ray imaging on-going display 43 that turns on when the X-ray is being irradiated; an instrument preparation display 45 that turns on when the X-ray imaging preparation is carried out; a warning display 47 that turns on when the instrument 1 does not function normally; and a malfunction display 49 that turns on when a malfunction in radiating the X-ray occurs. The X-ray photograph of the target area of the patient is taken while operating these switches.

A hand-switch 21 shown in FIG. 1, for example, is a two-stage type switch in which the operator pushes a button portion in two steps. First, the operator pushes the button portion into the first step to direct the instrument 1 to prepare for the X-ray irradiation. Then, the operator pushes the button portion further into the second step to start the instrument 1 to irradiate the X-ray.

Figure 4:
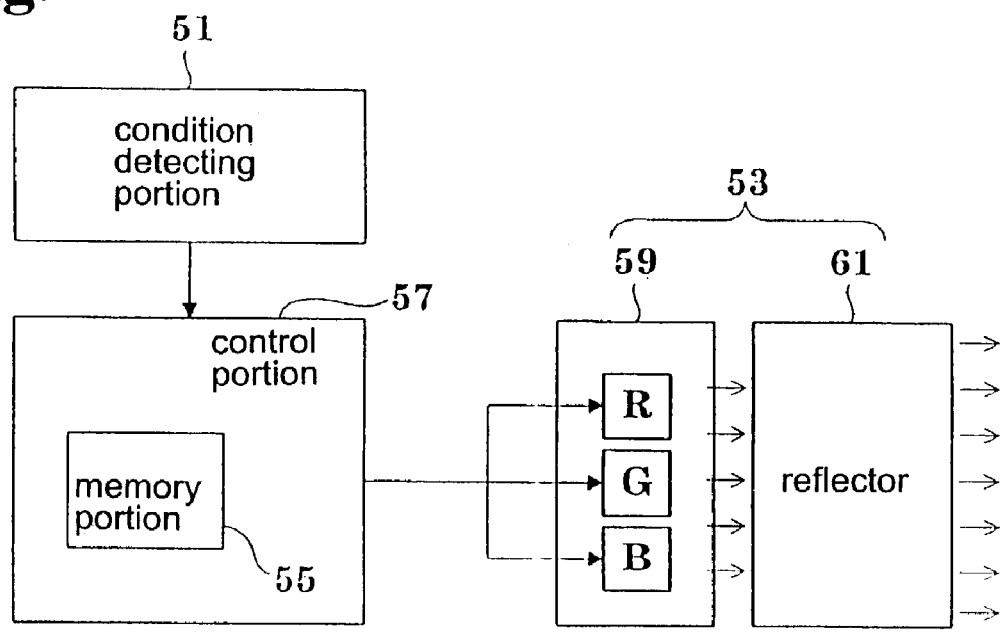
FIG. 4 is a block diagram showing a process of controlling a display portion of the X-ray diagnostic instrument.
Figure 5:
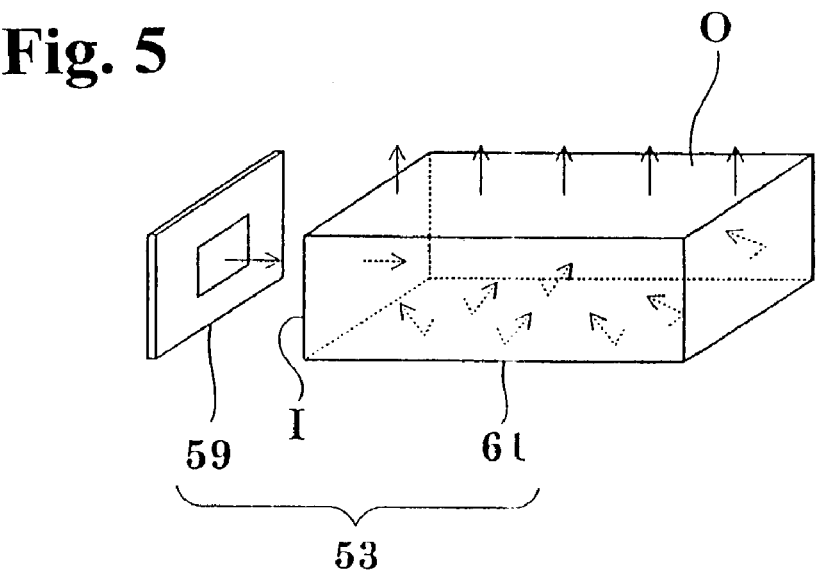
FIG. 5 is a perspective view showing a structure of the display portion of the X-ray diagnostic instrument.

A structure of one of characteristic portions of the present embodiment will be explained with reference to FIGS. 4 and 5. FIG. 4 is a block diagram showing a process of controlling the display portion of the X-ray diagnostic instrument. FIG. 5 is a perspective view showing a structure of the display portion of the X-ray diagnostic instrument.

As shown in FIG. 4, the X-ray instrument 1 of the present embodiment includes a condition detecting portion 51 for detecting a condition of the X-ray instrument 1; a display portion 53 for displaying light in multicolor and flushing light; a memory portion 55 for storing predetermined display mode data of the display portion 53 for each condition of the X-ray instrument 1; and a display control portion 57 for controlling the display portion 53 based on the display mode data stored in the memory portion 55 corresponding to the detected result from the condition detecting portion 51. Hereunder, the respective constituting portions will be explained specifically.

The condition detecting portion 51 detects conditions of the X-ray instrument 1 including, for example, a condition relating to an X-ray imaging of an X-ray imaging system (for example, the X-ray tube device 3 and the like), an extended/housed condition of the X-ray imaging system, or an abnormal condition of the X-ray instrument.

The condition relating to the X-ray imaging of the X-ray imaging system (for example, the X-ray tube device 3 and the like) includes an X-ray imaging preparation completion in which the X-ray imaging preparation is completed; an invalid operation condition in which the X-ray imaging preparation completion is released or in which no X-ray irradiation instruction is made within a predetermined time after the X-ray imaging preparation completion condition; an X-ray imaging on-going condition in which the X-ray is irradiated; and an X-ray irradiation completion condition in which the X-ray irradiation is completed. These conditions can be detected through monitoring, or detecting conditions of the X-ray tube device 3, the hand-switch 21 and the like.

The extended/housed condition of the X-ray imaging system includes a housed condition and an arm released (extended) condition. The housed condition is a state that the arm 29 is lowered and fits in an arm connecting portion 31. In the housed condition, the X-ray instrument 1 can be moved. The released condition is a state that the arm 29 is released from the arm connecting portion 31 and elevated. In the released condition, the X-ray imaging can be carried out.

The arm connecting portion 31 is provided with, for example, a micro-switch for detecting that the arm connecting portion 31 fits in the fitting portion (not shown) of the arm 29, in other words, that the arm 29 is in the housed condition.

The abnormal condition of the X-ray instrument 1 includes a condition in which the X-ray instrument 1 can not function normally, and the X-ray can not be irradiated. These conditions can be detected through monitoring (detecting a condition of) devices, such as the X-ray imaging system, the carrying system and the power supply system (charging system) of the X-ray tube device 3 and the like.

Further, as shown in FIG. 1, the X-ray instrument 1 of the present embodiment includes display portions 53 for displaying light in multicolor and flushing at a predetermined position (refer to FIG. 2) on an inclined surface near the X-ray control panel 7 of the cover 11 and a predetermined position on a front surface of the collimator 5, respectively. The display surfaces of the display portions 53 are disposed so as to be visible in a horizontal direction, thereby providing excellent visibility.

As shown in FIG. 5, the display portion 53 includes a multicolor emission LED (multicolor emission diode) 59 as a multicolor light emission source, and a reflector 61.

The multicolor emission LED 59 includes an R emitting portion for emitting red light, a G emitting portion for emitting green light, a B emitting portion for emitting blue light when an electrical current with a predetermined value is supplied. Accordingly, the multicolor emission LED 59 generates red light and green light when the electrical currents with the predetermined values are supplied to the R emitting portion and the G emitting portion, respectively. Also, yellow light can be obtained through mixing the red light generated from the R emitting portion and the green light generated from the G emitting portion. Further, other colors can be obtained by suitably adjusting the current value, duty and the like supplied to the respective emitting portions.

The light generated from the multicolor emission LED 59 is introduced into the reflector 61 through an incidence surface I. The reflector 61 reflects the light randomly to diffuse, so that a whole emission surface O emits the light and is brightened. The light enters and goes out only through the incidence surface I and the emission surface O shown in FIG. 5. A material for the reflector 61 includes, for example, a glass fiber and a rubber with a high transparency, however other materials may be used. As described above, the light is generated from a point light source, i.e. the multicolor emission LED 59, and introduced into the reflector 61. Then, the light is diffused inside the reflector 61, so that a surface light source, i.e. the emission surface O of the reflector 61, emits the light. In other word, the point light emission is converted to the surface light emission, so that the emission surface O (a display surface having a size sufficiently visible) can be lighted.

The memory portion 55 stores the predetermined display mode data of the display portion 53 for the respective conditions of the X-ray instrument 1. The display mode data includes, for example, data for the display portion 53 to display no light (no lighting) when the arm is housed; data for displaying the blue light when the arm is released; data for displaying the green light when the X-ray imaging preparation is completed; data for displaying the yellow light when the X-ray imaging is on-going; data for the display portion 53 to flush the blue light when the X-ray irradiation is completed; and data for displaying the red light when the X-ray imaging system such as the X-ray tube device 3, traveling system or power supply system (charging system) is in error (an abnormal condition of the X-ray instrument).

The display control portion 57 controls the display portion 53 based on the display mode data stored in the memory portion 55 corresponding to the result detected by the condition detecting portion 51. Specifically, for example, when the condition detecting portion 51 detects the arm released condition, the display control portion 57 controls the display portion 53 to display the blue light based on the display mode data stored in the memory portion 55 that instructs the display portion 53 to display the blue light.

Incidentally, the condition detecting portion 51 corresponds to condition detecting means of the invention; the display portion 53 corresponds to display means of the invention; the memory portion 55 corresponds to memory means of the invention; and the display control portion 57 corresponds to control means of the invention. Also, the condition detection of the instrument 1 by the condition detecting portion 51 corresponds to a condition detecting process of the invention; and the display control of the display portion 53 based on the result from the display control portion 57 corresponds to a control process of the invention.

Figure 6:
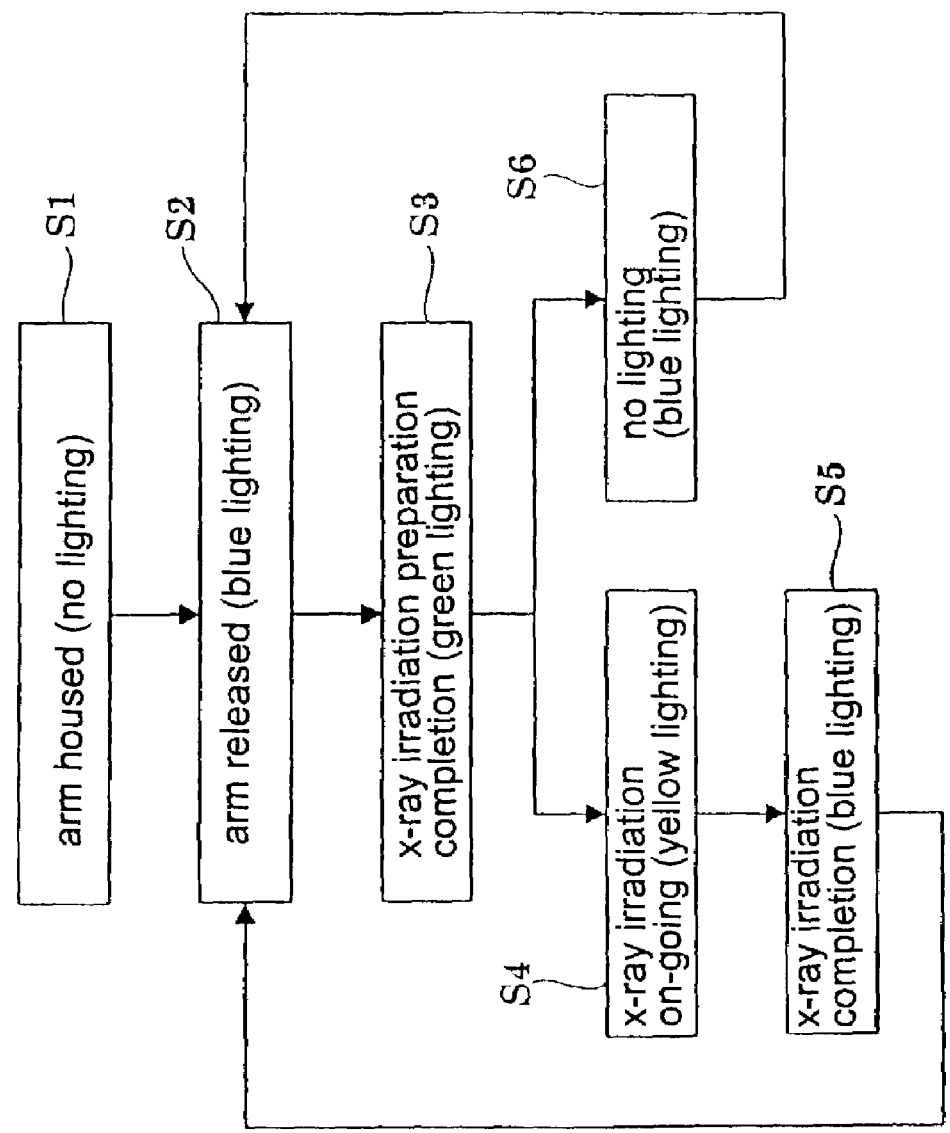
FIG. 6 is a flow chart showing a process of changing a display mode of the display portion according to a condition of the X-ray diagnostic instrument.

Next, a process of displaying the display portion 53 according to the conditions of the instrument 1 having the structure described above will be specifically explained with reference to FIG. 6. FIG. 6 is a flow chart showing a process of changing the display mode of the display portion according to the conditions of the instrument.

In Step S1 shown in FIG. 6, in a case that the arm 29 of the instrument 1 is in the housed condition, the condition detecting portion 51 detects the condition. Then, the display control portion 57 receives the display mode data (instructing the display portion 53 to display no light) stored in the memory portion 55 corresponding to the detected result (the arm housed condition) from the condition detecting portion 51 to thereby display no light.

In Step S2, the condition detecting portion 51 detects the arm released condition, when, for example, an operator moves the instrument 1 in the arm housed condition toward a patient, fixes the instrument by a brake (not shown) at a desired location, and releases the arm 29 to position the X-ray tube device 3 over the target area of the patient placed on the cassette. Accordingly, the display control portion 57 receives the display mode data (instructing the display portion 53 to display the blue light) stored in the memory portion 55 corresponding to the result (the arm released condition) detected by the condition detecting portion 51 to thereby display the blue light.

In Step S3, the operator stays away from the instrument 1 while holding the hand-switch 21, and presses the button portion of the hand-switch 21 to the first step, thereby instructing to start the X-ray irradiation preparation. When the X-ray irradiation preparation is completed, the condition detecting portion 51 detects the X-ray imaging preparation completion. Then, the display control portion 57 receives the display mode data (instructing the display portion 53 to display the green light) stored in the memory portion 55 corresponding to the result (the X-ray imaging preparation completion) detected by the condition detecting portion 51 to thereby display the green light.

In Step S4, the operator further presses the button portion to start the X-ray irradiation. The condition detecting portion 51 detects the X-ray irradiation on-going condition, and the display control portion 57 receives the display mode data (instructing the display portion 53 to display the yellow light) stored in the memory portion 55 corresponding to the result (the X-ray irradiation on-going condition) detected by the condition detecting portion 51 to thereby display the yellow light while the X-ray is being irradiated.

In Step S5, when the X-ray irradiation is completed, the condition detecting portion 51 detects the X-ray irradiation completed condition, and the display control portion 57 receives the display mode data (instructing the display portion 53 to flush the blue light for a predetermined period of time aid thereafter display the blue light) stored in the memory portion 55 corresponding to the result (the X-ray irradiation completed condition) detected by the condition detecting portion 51 to thereby flush the blue light for a predetermined period of time and thereafter to display the blue light.

In Step S6, in a case that the operator releases the button portion of the hand-switch 21 from the first step, or does not press the button portion of the hand-switch 21 to the second step for a predetermined period of time in the Step S3, the condition detecting portion 51 detects the operation invalid condition. The display control portion 57 receives the display mode data (instructing the display portion 53 to display the blue light) stored in the memory portion 55 corresponding to the result (the operation invalid condition) detected by the condition detecting portion 51 to thereby display the blue light.

When the X-ray instrument 1 is in the abnormal condition as described above, i.e. the X-ray instrument 1 does not function normally, or the X-ray instrument 1 fails to irradiate the X-ray, the condition detecting portion 51 detects the abnormal condition. The display control portion 57 receives the display mode data (instructing the display portion 53 to display the red light) stored in the memory portion 55 corresponding to the result (the abnormal condition) detected by the condition detecting portion 51 to thereby display the red light.

In the instrument 1 as described above, the condition detecting portion 51 detects the conditions of the X-ray instrument; the display portions 53 display the light in multicolor and flushes; the memory portion 55 stores the predetermined display mode data of the display portions 53 for every condition of the X-ray instrument 1; and the display control portion 57 controls the display portions 53 based on the display mode data stored in the memory portion 55 corresponding to the result detected by the condition detecting portion 51. Accordingly, the conditions of the X-ray instrument 1 can be displayed based on the display mode of the display portions 53, i.e. multicolor and flushing, so that the operator can instantly recognize the conditions of the X-ray instrument 1 precisely even from a location away from the instrument 1 by watching the color or the flushing of the display portions 53.

Specifically, the condition detecting portion 51 can detect the condition relating to the X-ray imaging of the X-ray imaging system; the extended/housed condition of the X-ray imaging system; and the abnormal condition of the X-ray instrument 1, as the condition of the X-ray diagnostic instrument. The display portions 53 can display the condition relating to the X-ray imaging of the X-ray imaging system, the extended/housed condition of the X-ray imaging system and the abnormal condition of the X-ray instrument as one of the display modes, i.e. color and flushing. Therefore, the operator can instantly recognize the condition of the X-ray instrument 1 precisely even from a location away from the instrument 1 by watching the color and flushing of the display portions 53.

Also, the display portions 53 are arranged so that the display surfaces thereof can be seen in the horizontal direction. Thus, the display surfaces of the display portions 53 have an excellent visibility.

The present invention is not limited to the above embodiment, and modifications as described below can be made.

In the instrument, as shown in FIG. 3, the X-ray control panel 7 includes the X-ray imaging preparation completion display 41, the X-ray imaging on-going display 43, the instrument preparation display 45, the warning display 47 and the error display 49. However, since the display portions 53 display the conditions of the instrument 1, a space of the X-ray control panel 7 may be minimized by removing the X-ray imaging preparation completion display 41, the X-ray imaging on-going display 43, the instrument preparation display 45, the warning display 47 and the error display 49.

In the instrument, the display portions 53 display the conditions of the instrument 1 by the colors and the flushing of the light. Alternatively, the display portions 53 display the conditions of the instrument 1 only by changing the colors, or only by displaying and flushing single color light. For example, as an example of using only the single color light, the display portions 53 may display the single color light for the arm released condition; the display portions 53 may flush the light for the X-ray irradiation preparation completion condition; and the display portions 53 may not display the light (no lighting) for the arm housed condition. Also, the other conditions of the instrument 1 may be displayed by changing an interval of the flushing.

In the instrument 1, the display portions 53 are provided at the cover 11 and the collimator 5 of the X-ray instrument 1. However, the positions of the display portions 53 are not limited thereto, and the display portions 53 may be disposed at any suitable positions.

In the instrument, the reflectors 61 are provided at the surface of the cover 11 and the surface on the front side of the collimator 5 of the X-ray instrument 1, respectively. However, a track ball may be provided to, for example, the X-ray control panel 7 or the like, as the reflectors 61, to allow the track ball to display the light in multicolor or flush.

In the instrument, while the hand switch 21 is employed, other input operation devices, such as a remote controller, may be employed so that the X-ray instrument 1 can be remotely controlled.

Although the instrument is used as the X-ray instrument 1, the X-ray diagnostic instrument according to the present invention is not limited to such an X-ray instrument. Alternatively, the invention can be applied to, for example, various X-ray imaging instruments, such as an X-ray transmission imaging apparatus.

As apparent from the above explanation, according to the X-ray diagnostic instrument of the present invention, the condition detecting device detects the conditions of the X-ray diagnostic instrument; the display device displays the light in multicolor or flushing the light; the memory device stores the predetermined display mode data of the display device for every condition of the X-ray diagnostic instrument; and the control device controls the display device based on the display mode data stored in the memory device corresponding to the results detected by the condition detecting device. Therefore, the conditions of the X-ray diagnostic instrument can be displayed by the display mode of the display device, i.e. the color or flushing of the display device, so that the operator can recognize precisely the conditions of the X-ray diagnostic instrument instantly even from a location away from the X-ray diagnostic instrument.

While the invention has been explained with reference to the specific embodiments of the invention, the explanation is illustrative and the invention is limited only by the appended claims.

What is claimed is:

1. An X-ray diagnostic instrument for taking an X-ray photograph through an X-ray imaging operation of an X-ray imaging system, comprising:
    an X-ray tube device,
    condition detecting means for detecting conditions of the X-ray diagnostic instrument,
    display means for displaying light by at least one of multicolor and flashing, said display means including a multicolor emission device containing therein a red light emitting portion, a green light emitting portion and a blue light emitting portion, and a reflector having an incidence surface attached to the multicolor emission device for receiving light from the multicolor emission device and an emission surface for emitting light therefrom so that the light emitted from the multicolor emission device is reflected and emitted through the emission surface,
    memory means for storing display mode data for the display means corresponding to the conditions of the X-ray diagnostic instrument, and
    control means electrically connected to the condition detecting means, display means and memory means for controlling the display means based on the display mode data corresponding to a result detected by the condition detecting means.

2. An X-ray diagnostic instrument according to claim 1, wherein said condition detecting means detects at least one of conditions relating to the X-ray imaging operation of the X-ray imaging system, a position of the X-ray imaging system, and an abnormal situation of the X-ray diagnostic instrument.

3. An X-ray diagnostic instrument according to claim 1, wherein said display means has the emission surface visible in a horizontal direction.

4. An X-ray diagnostic instrument according to claim 2, wherein said condition detecting means monitors an X-ray tube device and a hand switch of the X-ray diagnostic instrument to detect a condition relating to the X-ray imaging of the X-ray imaging system.

5. An X-ray diagnostic instrument according to claim 2, wherein said condition detecting means monitors a micro switch disposed in the X-ray imaging system to detect the condition relating to the position of the X-ray imaging system.

6. An X-ray diagnostic instrument according to claim 2, wherein said condition detecting means monitors at least one of the X-ray imaging system, a cart for carrying the X-ray diagnostic instrument, and a power supply of the X-ray diagnostic instrument to detect the condition relating to the operation of the X-ray diagnostic instrument.

7. An X-ray diagnostic instrument according to claim 1, wherein said reflector reflects the light randomly to diffuse so that the emission surface emits the light as a whole.

8. An X-ray diagnostic instrument according to claim 7, further comprising a collimator for forming X-ray, and an X-ray control panel, one display means being situated adjacent the X-ray control panel and one display means being situated adjacent the collimator.

* * * * *